United States Patent [19]

Merger et al.

[11] 4,408,079

[45] Oct. 4, 1983

[54] PREPARATION OF ALPHA-ALKYLACROLEINS

[75] Inventors: Franz Merger, Frankenthal; Hans-Juergen Foerster, Bobenheim-Roxheim, both of Fed. Rep. of Germany

[73] Assignee: BASF Aktiengesellschaft, Fed. Rep. of Germany

[21] Appl. No.: 339,505

[22] Filed: Jan. 15, 1982

[30] Foreign Application Priority Data

Feb. 21, 1981 [DE] Fed. Rep. of Germany ....... 3106557

[51] Int. Cl.$^3$ .............................................. C07C 47/22
[52] U.S. Cl. ..................................... 568/463; 568/461
[58] Field of Search ................................ 568/463, 461

[56] References Cited

U.S. PATENT DOCUMENTS

| 2,518,416 | 8/1950 | Bortnick | 260/601 |
|---|---|---|---|
| 2,639,295 | 5/1953 | Hagemeyer, Jr. | 260/530 |
| 2,848,499 | 8/1958 | MacLean et al. | 260/601 |
| 4,283,564 | 8/1981 | Bernhagen et al. | 568/463 |

FOREIGN PATENT DOCUMENTS

| 875194 | 4/1953 | Fed. Rep. of Germany | 568/463 |
|---|---|---|---|
| 2855504 | 12/1978 | Fed. Rep. of Germany | 568/463 |

OTHER PUBLICATIONS

Russ. Chem. Rev. 33 (1964), pp. 311–317.

*Primary Examiner*—Werren B. Lone
*Attorney, Agent, or Firm*—Keil & Witherspoon

[57] ABSTRACT

α-Alkylacroleins are prepared by reacting an alkanal with formaldehyde and a secondary amine in the presence of a carboxylic, dicarboxylic or polycarboxylic acid in certain molar ratios within a pH range of from 2.5 to 7 and at from 0° to 150° C.

The α-alkylacroleins which can be prepared by the process described are valuable starting materials for dyes, drugs and pest control agents.

10 Claims, No Drawings

PREPARATION OF ALPHA-ALKYLACROLEINS

The present invention relates to a process for the preparation of α-alkylacroleins by reacting an alkanal with formaldehyde and a secondary amine in the presence of a carboxylic, dicarboxylic or polycarboxylic acid in certain molar ratios within a pH range of from 2.5 to 7 and at from 0° to 150° C.

It is known that α-alkylacroleins can be prepared by Mannich condensation of an n-alkanal and formaldehyde with the aid of a secondary amine:

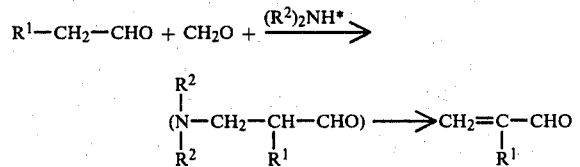

The reaction is generally carried out at above 40° C., under pressures of from 1 to 10 bar and at pH <3. The alkanal undergoes condensation with formaldehyde in $(R^2)_2NH$ to give the Mannich base, splitting of which gives the α-alkylacrolein and liberates the amine, which advantageously frequently forms a salt, with a strong acid (HCl, HBr, $H_2SO_4$, $H_3PO_4$ or a sulfonic acid), which catalyzes the reaction.

Methacrolein and 2-ethylacrolein can thus be prepared from propionaldehyde and n-butyraldehyde, respectively, and formaldehyde by the process disclosed in German Pat. No. 875,194. The Examples mention monocarboxylic acids, such as butyric acid and stearic acid. Molar ratios of propionaldehyde:formaldehyde=1:1.02, of propionaldehyde:secondary amine=1:0.038, of propionaldehyde:acid=1:0.013, and of secondary amine:acid=3:1, residence times of from 4 to 6 hours and boiling points of not more than 100° C. are mentioned. The process is generally carried out at pH <7.

In a similar process (German Laid-Open Application DOS No. 2,855,504) for the preparation of methacrolein, carboxylic acids, namely formic acid, acetic acid and especially propionic acid, and, as secondary amines, dipropylamine, methybutylamine, ethylbutylamine and, especially, di-n-butylamine are preferred. In the Example, a yield of only 81.7% is achieved in 120 minutes in a reaction at from 30° to 100° C. under 2.5 bar. Molar ratios of propionaldehyde:formaldehyde=1:1-1.5, of propionaldehyde:secondary amine=1:0.02-0.05 (1:0.025), and of propionaldehyde:acid=1:0.01-0.02 (1:0.015) are prescribed.

Both publications mention a catalytic amount of an amine together with use of a carboxylic acid. A satisfactory reaction rate is still achieved by reaction at pH<7 (excess of strongly basic amine relative to RCOOH) at relatively high temperatures, so that dimerization of the alkylacrolein is still of no great importance. However, as our own experiments show (see Comparative Examples 6 and 7), the yields are difficult to reproduce, since, besides methylacrolein, a substantial amount of other aldol condensation products (2-methylpentenal and methylol compounds) is also always obtained.

U.S. Pat. No. 2,518,416 discloses the condensation of an alkanal and formaldehyde in a molten salt $(R^2)_2NH.HX$ (HX=an acid with an acidity not less than that of trichoroacetic acid), preferably in $(CH_3)_2NH.HCl$, at from 120° to 300° C., preferably from 140° to 220° C. Example 1 mentions a yield of 51% of ethylacrolein from n-butyraldehyde and formaldehyde at from 200° to 220° C.

U.S. Pat. No. 2,639,295 discloses the condensation of propionaldehyde and formaldehyde in a ratio of 2-6:1 in the presence of not more than 0.25 equivalent of $(R^2)_2NH.HX$ ($(R^2)_2NH$=secondary amine; HX=in particular, HCl, HBr, $H_2SO_4$ or $H_3PO_4$) at from 80° to 130° C. and at pH 4-6, virtually all the aldehyde being continuously distilled off as an azeotrope. The optimum yield (Example 8) of 92.5%, based on formaldehyde, is achieved with a molar ratio of propionaldehyde:formaldehyde of 5:1 and a 10 percent strength acetic acid solution of piperidine.HCl.

The main reason for deactivation of the catalyst $(R^2)_2NH$, accompanied by decreasing selectivity, is its methylation to $R^2NCH_3$, ie. to a catalytically inactive tertiary amine (Leuckardt-Wallach reaction, cf. HoubenWeyl, Volume 11/1 (1957), pages 648-654). U.S. Pat. No. 2,639,295 therefore proposes using an excess of propionaldehyde, but this is uneconomical because of the large amount of material circulating, and provides the higher selectivity in respect of formaldehyde at the expense of unavoidable losses of propionaldehyde, interalia by condensation to methylpentenal. The proposed regeneration of the catalyst by heating it at from 150° to 300° C. is ineffective in respect of the inactive tertiary amine $R^2NCH_3$ formed. The irreversible consumption of the catalyst is, however, a contributory disadvantage of the economics of a process for the preparation of α-alkylacroleins by Mannich condensation. Because of its mineral acid content, working up or disposal of spent catalyst mixed with by-products from the synthesis is extremely expensive and environment-polluting.

U.S. Pat. No. 2,848,499 discloses a similar process for continuous condensation of propionaldehyde/formaldehyde/$(R^2)_2NH.HX$ in a ratio of 1:1.2-5 at from 105° to 120° C. under superatmospheric pressure. The acids mentioned are HCl, $H_2SO_4$, $H_3PO_4$ and acetic acid. The only Example described uses HCl, and indicates that, with a ratio of propionaldehyde:formaldehyde:$(CH_3)_2NH.HCl$ of just 1:1.036:2.5 at 111° C., a conversion of 98.1% of propionaldehyde and a selectivity of 99.6%, based on propionaldehyde, or 99%, based on formaldehyde, are achieved. A large excess of amine salt is used in the process, and this is also uneconomical because of the large amount of material circulating; moreover, if the preferred catalyst dimethylamine hydrochloride is used, the problems described above in respect of working up or disposal also arise here.

Russ. Chem. Rev. 33 (1964), 314 discloses the condensation of propionaldehyde, formaldehyde and $(C_2H_5)_2NH.HCl$ in a ratio of 1.1:1:1 at pH 6-7 and 45° C. for 20 minutes. The liberation of methylacrolein at 45° C. permits production without substantial by-product formation. In contrast, substantial amounts of "polymers" and low yields are said to be obtained at the higher temperature necessary with a catalytic amount, namely 0.1 mole, of $(R^2)_2NH$/mole of formaldehyde. A marked dependence on the pH was found: it is stated that in contrast to the situation at pH 3-4 (where the reaction has to be carried out at from 100° to 120° C.), at the optimum pH of 6-7 the reaction can be carried out at such a low temperature that high selectivities can be achieved without polymerization losses. It is expressly stated that "in contrast, prior art processes employ far from optimum conditions." Varying yields which are difficult to reproduce or unsatisfactory result. The authors thus underline the importance of the conditions.

Relatively cheap low molecular weight amines (with a high NH content) are preferably used in the last four processes mentioned. However, simple distillation then gives α-alkylacroleins, such as methylacrolein or 2-ethylacrolein, with substantial amine contents, so that expensive refining is as a rule indispensable for further processing. Additional amine losses during concentration of the catalyst mixture, after the methylacrolein produced has been isolated, by distilling off the water of reaction and the water introduced with the formaldehyde are greater, the more volatile the amine employed.

All the processes mentioned are unsatisfactory in that they do not simultaneously achieve the optimum in respect of yield, catalyst consumption and simplicity of operation; the processes disclosed in German Pat. No. 875,194 and German Laid-Open Application DOS No. 2,855,504 are not sufficiently selective, and the consumption of amine is significant; the processes disclosed in U.S. Pat. Nos. 2,518,416, 2,639,295 and 2,848,499 are technologically very complicated (large excesses of individual components, and difficult conditions) and/or give poor results; and whilst the Russian process gives good yields in a technically simple manner, it has substantial disadvantages; toxicity problems exclude the use of the recommended catalyst $(C_2H_5)_2NH \cdot HCl$; the product is of inferior quality because of the amine content; catalyst consumption is substantial, the disposal of inorganic/organic waste products is difficult and moreover $NR_2H \cdot HCl$ is highly corrosive.

We have now found that α-alkylacroleins of the formula

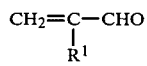

where $R^1$ is an aliphatic radical, are advantageously prepared by reacting an alkanal of the formula

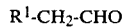

where $R^1$ has the above meaning, with formaldehyde and a secondary amine in the presence of an acid, by a process wherein the reaction is carried out with a molar ratio of starting material II to formaldehyde of 0.9–1.5:1, at a pH of 2.5–7 and at from 0° to 150° C. in the presence of (a) from 0.05 to 1.5 equivalents of an aliphatic monocarboxylic acid of 2 to 10 carbon atoms per mole of starting material II or
(b) from 0.01 to 1.5 equivalents of a dicarboxylic or polycarboxylic acid of 2 to 10 carbon atoms per mole of starting substance II, as the acid, and in the presence of a secondary amine, using an equivalent ratio of carboxylic acid to amine of 1–2:1.

If propionaldehyde is used, the reaction can be represented by the following equation:

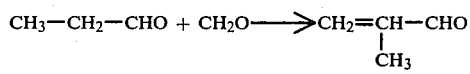

The present invention is based on the observation that a useful process must take into consideration not only the yield but also other results of the reaction, some of which are even more important. Compared to the prior art, the process according to the invention gives a combination of comparatively excellent results, for example high selectivity in respect of both components (alkanal and formaldehyde), coupled with almost quantitative conversion, a high space/time yield, a high catalyst efficiency expressed as Q=moles of α-alkylacrolein/equivalent of secondary amine, a product of good quality (which can be directly processed further), technical simplicity, no serious toxicity problems and economically efficient ecologically acceptable disposal of waste products. In view of the conventional processes, all these results are surprising.

The process is, particularly, surprisingly, superior to the conventional methods because of its relatively high catalyst efficiency Q. While secondary amines in combination with mineral acids, eg. sulfuric acid, have Q values of ≈20 moles/equivalent of secondary amine in reactions of n-alkanals with formaldehyde, they give Q values of from 60 to 70 moles/equivalent of secondary amine if they are used together with dicarboxylic or polycarboxylic acids. This permits technically and economically advantageous production of highly pure α-alkylacroleins and is therefore, inter alia, especially useful in the production of methacrolein, which is particularly useful, even in the form of the crude distillate (with a water content of from 2 to 3%), for the preparation of methacrylic acid by oxidation with $O_2$.

The alkanal can be reacted with formaldehyde in stoichiometric amount, in less than this amount or in excess, for example in an amount of from 0.9 to 1.5, preferably from 0.95 to 1.2 and especially from 1.0 to 1.10, moles of starting material II per mole of formaldehyde. Preferred starting materials II and accordingly preferred end products I are those where $R^1$ is alkyl of 1 to 8 carbon atoms. The above radicals can also be substituted by groups which are inert under the reaction conditions, eg. alkoxy or alkyl of 1 to 4 carbon atoms.

Examples of starting materials II are thus propanal, n-butanal, 3-methylbutanal, n-pentanal, 3-methylhexanal, 3-ethylpentanal, 4-methylhexanal, n-heptanal, n-nonanal and n-decanal.

The formaldehyde is advantageously used in aqueous solution, preferably in 20–60 percent strength by weight solution. Aliphatic monocarboxylic, dicarboxylic and polycarboxylic acids of from 2 to 10 carbon atoms are used as the acids. The dicarboxylic acids and polycarboxylic acids (preferably tricarboxylic acids) may also be aromatic or araliphatic carboxylic acids. Dicarboxylic and polycarboxylic acids are more advantageous than monocarboxylic acids. Examples of suitable acids are acetic acid, propionic acid, methoxyacetic acid, the butyric acids, pentanoic, hexanoic, heptanoic, octanoic, nonanoic and decanoic acid, pivalic acid, 2-ethylbutyric acid, 2-methylpentanoic acid, 2-ethylhexanoic acid and isononanoic acid; pimelic acid, suberic acid, azelaic acid, sebacic acid, nonanedicarboxylic acid, decanedicarboxylic acid, pentane-1,3,5-tricarboxylic acid, 3-hydroxyglutaric acid, saccharic acid, α,α'-dihydroxyadipic acid and, preferably, succinic acid, glutaric acid, adipic acid, malic acid, tartaric acid, butane-1,2,4-tricarboxylic acid, 3-ethylpentane-1,3,5-tricarboxylic acid, citric acid, trimellitic acid, butanetetracarboxylic acid, pyromellitic acid, phthalic acid, terephthalic acid, isophthalic acid and fumaric acid, and, particularly preferably, oxalic acid.

Advantageous amines are those of the formula

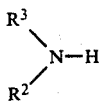   III where $R^3$ and $R^2$ can be identical or different and each is alkyl of 1 to 12, advantageously of 1 to 10 and preferably of 1 to 6, carbon atoms, advantageously substituted by one or more hetero-atoms, preferably by hydroxyl and/or secondary or tertiary amino, or $R^2$ and $R^3$, together with the adjacent carbon atom, are members of an advantageously 5-membered or 6-membered ring, which may also contain a nitrogen or oxygen atom. $R^2$ can also be

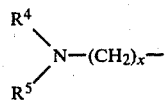

where $R^4$ and $R^5$ can be identical or different and each is alkyl of 2 to 18, advantageously of 2 to 10 and preferably of 2 to 6, carbon atoms which is unsubstituted or substituted by several, advantageously two and preferably one, hydroxyl group, and $R^4$ can also be H, and x is a number from 2 to 6. In monohydroxyalkyl radicals, the hydroxyl group is advantageously in the ω-position. Secondary amines with a boiling point of not less than 130° C. are preferred. Secondary amines which have a very low volatility, such as, for example, the hydroxyalkylamines which can easily be obtained, for example, from ammonia or a primary amine and an alkylene oxide, or amines with two or more amino groups, at least one of which is a secondary amino group, the others being secondary and/or tertiary groups, are particularly preferred.

Amines III which can be used therefore include N-methyl-, N-ethyl-, N-propyl-, N-isopropyl-, N-butyl-, N-isobutyl-, N-sec.-butyl-, N-tert.-butyl-, N-pentyl-, N-hexyl-, N-heptyl-, N-octyl-, N-nonyl- and N-decyl-(hydroxyethylamine); corresponding amines which are disubstituted by identical or different substituents chosen from those above; piperidine, morpholine, pyrrolidone, piperazine and N-methylpiperazine; N-ethyl-, N-propyl-, N-isopropyl-, N-butyl-, N-isobutyl-, N-sec.-butyl-, N-tert.-butyl-, N-pentyl-, N-hexyl-, N-heptyl-, N-octyl-, N-nonyl- and N-decyl-N-hydroxyethylamine; corresponding amines which are substituted by one of the above hydroxyl-free substituents and by hydroxypropyl or hydroxybutyl; amines which are disubstituted by identical or different hydroxyalkyl substituents chosen from those above, N,N,N'-triethanolethylenediamine, N,N'-diethanolethylenediamine and homologous dipropanol and tripropanol compounds, and corresponding propylenediamine and butylenediamine compounds. Methylhydroxyethylamine, ethylhydroxyethylamine, propylhydroxyethylamine, isopropylhydroxyethylamine, butylhydroxyethylamine, isobutylhydroxyethylamine, methylhydroxypropylamine, ethylhydroxypropylamine, propylhydroxypropylamine, isopropylhydroxypropylamine, butylhydroxypropylamine, isobutylhydroxypropylamine, dihydroxyethylamine, dihydroxypropylamine, N,N'-diethanolethylenediamine, piperazine, N-methylpiperazine and dibutylamine are preferred.

In the case of monocarboxylic acids, advantageously between 0.05 to 1.5, in particular from 0.06 to 1.4, preferably from 0.3 to 1.25 and especially from 0.6 to 1.1, equivalents of monocarboxylic acid and advantageously from 0.05 to 1.5, preferably from 0.3 to 1.25 and especially from 0.6 to 1.1, equivalents of amine are used per mole of starting material II. In the case of dicarboxylic or polycarboxylic acids, advantageously between 0.01 to 1.5, preferably from 0.05 to 1.5 and especially from 0.3 to 1.25, equivalents of dicarboxylic or polycarboxylic acid and advantageously from 0.01 to 1.5, preferably from 0.05 to 1.5 and especially from 0.3 to 1.25, equivalents of amine are used per mole of starting material II. The reaction is carried out with an equivalent ratio of carboxylic acid to amine of 1–2:1, preferably 1.05–1.8:1 and especially 1.1–1.5:1.

The reaction is carried out at pH 2.5–7, preferably 3–6.5 and especially 3–6, at from 0° C. to 150° C., advantageously from 20° to 130° C., preferably from 30° to 120° C. and especially from 40° to 110° C., and under atmospheric, superatmospheric or reduced pressure, continuously or batchwise. The water content in the starting mixture is advantageously from 20 to 80 percent by weight, preferably from 20 to 40 percent by weight.

The reaction can be carried out as follows: a mixture of starting material II, amine III, formaldehyde, water and acid is kept at the reaction temperature for 1–300 minutes, as a rule for 5–120 minutes and preferably for 10–90 minutes. The end product is then isolated from the reaction mixture in a conventional manner, for example by phase separation and/or distillation. The process can be carried out batchwise or continuously in various reactors (eg. stirred kettles, tube reactors). Thus, for batchwise preparation of an α-alkylacrolein, formaldehyde can first be introduced into the catalyst mixture which has been prepared from a secondary amine and a carboxylic acid and has a water content of 30–60 percent by weight, and the starting material II can then be added, or formaldehyde and an alkanal can be run simultaneously, together or in parallel, into the mixture and the mixture can then be allowed to react under the defined conditions. The end product I can be isolated from the mixture by phase separation and/or by batchwise or continuous distillation.

In the continuous procedure, the condensation is advantageously carried out in a cascade of 2–3 stirred kettles by simultaneously adding formaldehyde and an alkanal to the circulating catalyst mixture and continuously distilling off from the product mixture, together or in succession, the α-alkylacrolein and the $H_2O$ introduced with the formaldehyde and formed during the reaction. A proportion of catalyst mixture corresponding to the consumption of amine III is removed and is worked up or disposed of, for example by residue-free combustion.

The α-alkylacroleins which can be prepared by the process are valuable starting materials for dyes, drugs and pest control agents. Oxidation of the methacroleins gives the corresponding methacrylic acids and from these methacrylates are obtained which are valuable in the production of plastics, acrylic glass, molding materials, profiles, finishes, lubricating oils, adhesives and textile auxiliaries. Regarding the use of the products, reference may be made to the above publications and Ullmanns Encyklopädie der technischen Chemie (4th edition), Volume 16, pages 609 to 614.

In the Examples which follow, parts are by weight.

EXAMPLE 1

The amine salt is prepared from 1,125 parts of 40 percent strength by weight oxalic acid (5 moles) and 1,050 parts (10 moles) of diethanolamine. 750 parts of 40 percent strength by weight formaldehyde solution and 580 parts (10 moles) of propionaldehyde are then added at 20° C., and the reaction mixture is kept at from 40° to 50° C. for one hour. The crude end product contains 2.6 percent by weight of water and 0.8 percent by weight of organic impurities. 660 parts (94.3% of theory) of methacrolein of boiling point 68° C./1,013 mbar are obtained by azeotropic distillation.

EXAMPLE 2

The amine salt is prepared from 2,281 parts of 16 percent strength by weight aqueous adipic acid (2.5 moles) and 215 parts (2.5 moles) of piperazine. 375 parts of 40 percent strength by weight formaldehyde solution and 290 parts (5 moles) of propionaldehyde are then added at 20° C., and the reaction mixture is kept at from 40° to 50° C. for one hour. The crude end product contains 2.5 percent by weight of water and 0.8 percent by weight of organic impurities. 320 parts (91.4% of theory) of methacrolein of boiling point 68° C./1,013 mbar are obtained by distillation.

EXAMPLE 3

The amine salt is prepared from 1,181 parts of 40 percent strength by weight oxalic acid (5.25 moles) and 1,050 parts (10 moles) of diethanolamine. 750 parts of 40 percent strength by weight formaldehyde solution and 720 parts (10 moles) of n-butyraldehyde are then added at 20° C., and the reaction mixture is kept at from 40° to 50° C. for one hour. The crude end product contains 2.2 percent by weight of water and 1.2 percent by weight of organic impurities. 801 parts (95.4% of theory) of ethylacrolein are obtained by distillation.

EXAMPLE 4 (COMPARATIVE EXAMPLE)

The amine salt is prepared from 245 parts of 40 percent strength by weight sulfuric acid and 210 parts (2 moles) of diethanolamine. 300 parts of 40 percent strength by weight formaldehyde and 232 parts (4 moles) of propionaldehyde are then added at 20° C., and the reaction mixture is kept at from 40° to 50° C. for 2 hours. Thereafter, the methacrolein is first distilled off, followed by the water introduced with the formaldehyde and that formed during the reaction. A further 300 parts of 40 percent strength by weight formaldehyde and 232 parts of propionaldehyde are added to the catalyst solution thus recovered, and the mixture is left at from 40° to 50° C. for 2 hours. After the methacrolein and water have been distilled off, the same catalyst solution is used again. This procedure is repeated until the organic phase passing over during distillation has a methacrolein content of <90%. A total of 3,000 parts of methacrolein (calculated as 100 percent pure methacrolein) is thus obtained, corresponding to 21.4 moles of methacrolein/secondary amine equivalent.

EXAMPLE 5

The amine salt is prepared from 225 parts of 40 percent strength by weight oxalic acid and 210 parts (2 moles) of diethanolamine. 300 parts of 40 percent strength by weight formaldehyde and 232 parts (4 moles) of propionaldehyde are then added at 20° C., and the reaction mixture is kept at from 40° to 50° C. for 2 hours. Thereafter, the methacrolein is first distilled off, followed by the water introduced with the formaldehyde and that formed during the reaction. A further 300 parts of 40 percent strength by weight formaldehyde and 232 parts of propionaldehyde are added to the catalyst solution thus recovered, and the mixture is left at from 40° to 50° C. for 2 hours. After the methacrolein and water have been distilled off, the same catalyst solution is used again. This procedure is repeated until the organic phase passing over during distillation has a methacrolein content of <90%. A total of 8,880 parts of methacrolein (based on 100 percent pure methacrolein) is thus obtained, corresponding to 63.4 moles of methacrolein/secondary amine equivalent.

EXAMPLE 6 (COMPARATIVE EXAMPLE)

622 parts (10.7 moles) of propionaldehyde, 12 parts (0.16 mole) of propionic acid, 1,180 parts of 30 percent strength by weight formaldehyde (11.8 moles) and 35 parts (0.25 mole) of di-n-butylamine are mixed in an autoclave under nitrogen, during which process the temperature rises to 28° C. The mixture is then stirred at 100° C. for one hour, under an autogenous pressure of 2.4 bar. After the reaction mixture has been cooled, the two phases are separated and each phase is worked up by itself, by distillation. The crude end product contains 2.5 percent by weight of water and 7.3 percent by weight of organic impurities. 588 parts (78.5% of theory) of methacrolein of boiling point 68° C./1,013 mbar are obtained by distillation.

EXAMPLE 7 (COMPARATIVE EXAMPLE)

40 parts of sodium chloride and 4 parts of n-butyric acid are added to 350 parts of 30 percent strength by weight formaldehyde and 195 parts of propionaldehyde, and 6.5 parts of piperidine are added in the course of 2 hours. The mixture is then refluxed for a further 3 hours. After this period, 112 parts of organic material can be distilled off before the boiling point reaches 100° C. The crude end product contains 2.6 percent by weight of water and 19 percent by weight of organic impurities. 88 parts (37.4% of theory) of methacrolein of boiling point 68° C./1,013 mbar are obtained by distillation.

EXAMPLE 8 (COMPARATIVE EXAMPLE)

The amine salt is prepared from 245 parts of 40 percent strength by weight sulfuric acid and 210 parts (2 moles) of diethanolamine. 300 parts of 40 percent strength by weight formaldehyde and 288 parts (4 moles) of n-butyraldehyde are then added at 20° C., and the reaction mixture is kept at from 40° to 50° C. for 2 hours. Thereafter, the 2-ethylacrolein is first distilled off, followed by the water introduced with the formaldehyde and that formed during the reaction. A further 300 parts of 40 percent strength by weight formaldehyde and 288 parts of n-butyraldehyde are added to the catalyst solution thus recovered, and the mixture is left at from 40° to 50° C. for 2 hours. After the 3-ethylacrolein and water have been distilled off, the same catalyst solution is used again. This procedure is repeated until the organic phase passing over during distillation has a 2-ethylacrolein content of <90%. A total of 3,225 parts of 2-ethylacrolein (calculated as 100 percent pure 2-ethylacrolein) is thus obtained, corresponding to 19.2 moles of 2-ethylacrolein/secondary amine equivalent.

EXAMPLE 9

The amine salt is prepared from 1,500 parts of 40 percent strength by weight acetic acid (10 moles) and 1,050 parts (10 moles) of diethanolamine. 750 parts of 40 percent strength by weight formaldehyde solution (10 moles) and 580 parts (10 moles) of propionaldehyde are then added at 20° C., and the reaction mixture is kept at from 40° to 50° C. for one hour. The crude end product contains 2.6 percent by weight of water and 1.8 percent by weight of organic impurities. 643 parts (91.8% of theory) of methacrolein of boiling point 68° C./1,013 mbar are obtained by distillation.

EXAMPLE 10

The amine salt is prepared from 3,600 parts of 40 percent strength by weight 2-ethylhexanoic acid (10 moles) and 430 parts (5 moles) of piperazine. 750 parts of 40 percent strength by weight formaldehyde solution (10 moles) and 580 parts (10 moles) of propionaldehyde are then added at 20° C., and the reaction mixture is kept at from 40° to 50° C. for one hour. The crude end product contains 2.8% of water and 1.65% of organic impurities. 672 parts (96% of theory) of methacrolein of boiling point 68° C./1,013 mbar are obtained by distillation.

EXAMPLE 11

The amine salt is prepared from 2,420 parts of 40 percent strength by weight isobutyric acid (1 mole) and 430 parts (5 moles) of piperazine. 750 parts of 40 percent strength by weight formaldehyde solution (10 moles) and 580 parts (10 moles) of propionaldehyde are then added at 20° C., and the reaction mixture is kept at from 40° to 50° C. for one hour. The crude end product contains 2.6% of water and 1.45% of organic impurities. 666 parts (93.7% of theory) of methacrolein of boiling point 68° C./1,013 mbar are obtained by distillation.

EXAMPLE 12

The amine salt is prepared from 1,850 parts of 40 percent strength by weight propionic acid (10 moles) and 1,290 parts (10 moles) of dibutylamine. 750 parts of 40 percent strength by weight formaldehyde solution (10 moles) and 720 parts (10 moles) of n-butyraldehyde are then added at 20° C., and the reaction mixture is kept at from 40° to 50° C. for one hour. The crude end product contains 2.2 percent by weight of water and 1.2% of organic impurities. 795 parts (94.6% of theory) of α-ethylacrolein of boiling point 92° C. are obtained by distillation.

EXAMPLE 13

The amine salt is prepared from 2,900 parts of 40 percent strength by weight 2-methylpentanoic acid (10 moles) and 750 parts (10 moles) of methylhydroxyethylamine 750 parts of 40 percent strength by weight formaldehyde solution (10 moles) and 860 parts (10 moles) of 3-methylbutanal are then added at 20° C., and the reaction mixture is kept at from 40° to 50° C. for 2 hours. The crude end product contains 3.4 percent by weight of water and 2.8 percent by weight of organic impurities. 902 g (92% of theory) of isopropylacrolein of boiling point 108° C. are obtained by distillation.

EXAMPLE 14

The amine salt is prepared from 1,500 parts of 40 percent strength by weight acetic acid (10 moles) and 430 parts (5 moles) of piperazine. 750 parts of 40 percent strength by weight formaldehyde solution (10 moles) and 1,000 parts (10 moles) of n-hexanal are then added at 20° C., and the reaction mixture is kept at from 40° to 50° C. for 3 hours. The crude end product contains 0.6 percent by weight of water and 2.2 percent by weight of organic impurities. 1,047 parts (93.5% of theory) of n-butylacrolein of boiling point 125° C./1,013 mbar are obtained by distillation.

EXAMPLE 15

The amine salt is prepared from 973.3 parts of 15 percent strength by weight adipic acid and 86 parts (1 mole=2 equivalents) of piperazine. 300 parts of 40 percent strength by weight formaldehyde and 288 parts (4 moles) of n-butyraldehyde are then added at 20° C., and the reaction mixture is kept at from 40° to 50° C. for 2 hours. Thereafter, the 2-ethylacrolein is first distilled off, followed by the water introduced with the formaldehyde and that formed during the reaction. A further 300 parts of 40 percent strength by weight formaldehyde and 288 parts of n-butyraldehyde are added to the catalyst solution thus recovered, and the mixture is left at from 40° to 50° C. for 2 hours. After the 2-ethylacrolein and water have been distilled off, the same catalyst solution is used again. This procedure is repeated until the organic phase passing over during distillation has a 2-ethylacrolein content of <90%. A total of 11,190 parts of 2-ethylacrolein (calculated as 100 percent pure 2-ethylacrolein) is thus obtained, corresponding to 66.2 moles of 2-ethylacrolein/secondary amine equivalent.

EXAMPLE 16

The amine salt is prepared from 1,600 parts of 40 percent strength by weight glutaric acid (B 5 moles) and 1,290 parts (10 moles) of dibutylamine. 750 parts of 40 percent strength by weight formaldehyde solution and 1,000 parts (10 moles) of n-hexanal are then added at 20° C., and the reaction mixture is kept at from 40° to 50° C. for 3 hours. The crude end product contains 0.6 percent by weight of water and 3.1 percent by weight of organic impurities. 1,038 parts (92.7% of theory) of n-butylacrolein of boiling point 125° C./1,013 mbar are obtained by distillation.

EXAMPLE 17

986.7 parts of a 60 percent strength by weight aqueous solution of the salt of oxalic acid and diethanolamine (2 moles of oxalic acid and 4 moles of diethanolamine), 300 parts of 40 percent strength by weight formaldehyde solution and 232 parts (4 moles) of propionaldehyde per hour are pumped into a cascade consisting of 2 stirred vessels. The vessels are thermostatically controlled at 50° C., and the residence time is 1.27 hours. 1,518.7 parts per hour are removed from the second vessel and distilled continuously, 273.5 parts per hour of organic material and 254 parts per hour of water being obtained. The catalyst solution is concentrated to its original nitrogen content and recycled. The crude end product contains 2.4 percent by weight of water and 1.2 percent by weight of organic impurities. 263.7 parts per hour (94.2% of theory) of methacrolein of boiling point 68° C./1,013 mbar are obtained by disillation.

We claim:
1. A process for the preparation of an α-alkylacrolein of the formula

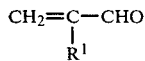

where $R^1$ is an aliphatic radical, by reacting an alkanal of the formula

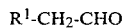

where $R^1$ has the above meaning, with formaldehyde and a secondary amine in the presence of an acid, wherein the reaction is carried out with a molar ratio of starting material II to formaldehyde of 0.9–1.5:1, at a pH of 2.5–7 and at form 0° to 150° C. in the presence of (a) between 0.05 and 1.5 equivalents of an aliphatic monocarboxylic acid of 2 to 10 carbon atoms per mole of starting material II or (b) between 0.3 and 1.25 equivalents of a dicarboxylic or polycarboxylic acid of 2 to 10 carbon atoms per mole of starting substance II, as the acid, and in the presence of a secondary amine, using an equivalent ratio of carboxylic acid to amine of 1–2:1.

2. The process as claimed in claim 1, wherein the reaction is carried out with 0.95 to 1.2 moles of starting material II per mole of formaldehyde.

3. The process as claimed in claim 1, wherein the reaction is carried out with from 0.06 to 1.4 equivalents of monocarboxylic acid and 0.05 to 1.5 equivalents of amine per mole of starting material II.

4. The process as claimed in claim 1, wherein the reaction is carried out with from 0.05 to 1.5 equivalents of dicarboxylic or polycarboxylic acid and from 0.01 to 1.5 equivalents of amine per mole of starting material II.

5. The process as claimed in claim 1, wherein the reaction is carried out with an equivalent ratio of carboxylic acid to amine of 1.05–1.8:1.

6. The process as claimed in claim 1, wherein the reaction is carried out at pH 3–6.5.

7. The process as claimed in claim 1, wherein the reaction is carried out at from 20° to 130° C.

8. The process of claim 1, wherein $R^1$ is an unsubstituted alkyl of 1 to 4 carbon atoms or an alkyl of 1 to 4 carbon atoms substituted by alkoxy or alkyl of 1 to 4 carbon atoms.

9. The process of claim 1, wherein $R^1$ is propanal, n-butanal, 3-methylbutanal, n-pentanal, 3-methylhexanal, 3-ethylpentanal, 4-methylhexanal, n-heptanal, n-nonanal or n-decanal.

10. The process of claim 1, wherein $R^1$ is propanal.

* * * * *